United States Patent [19]

Matsuura

[11] Patent Number: 4,860,731
[45] Date of Patent: Aug. 29, 1989

[54] ENDOSCOPE

[75] Inventor: Nobuyuki Matsuura, Hino, Japan

[73] Assignee: Olympus Optical Co., Ltd., Tokyo, Japan

[21] Appl. No.: 255,568

[22] Filed: Oct. 11, 1988

[30] Foreign Application Priority Data

Dec. 17, 1987 [JP] Japan .................. 62-322603

[51] Int. Cl.$^4$ ..................... A61B 1/06; A61B 1/12
[52] U.S. Cl. ..................................... 128/6; 128/4
[58] Field of Search ........................... 128/4, 6

[56] References Cited

U.S. PATENT DOCUMENTS

| 4,325,362 | 4/1982 | Ouchi et al. | 128/4 |
| 4,509,507 | 4/1985 | Yabe | 128/4 |
| 4,562,830 | 1/1986 | Yabe | 128/4 |
| 4,748,970 | 6/1988 | Nakajima | 128/4 |
| 4,760,838 | 8/1988 | Fukuda | 128/4 |
| 4,800,869 | 1/1989 | Nakajima | 128/4 |

Primary Examiner—William H. Grieb
Attorney, Agent, or Firm—Armstrong, Nikaido, Marmelstein, Kobovcik & Murray

[57] ABSTRACT

An endoscope having sucking tube lines large in the sucking capacity of the present invention has an insertable part to be inserted into a body cavity and is provided in the front end part of the insertable part with an illuminating window illuminating an observed part, an observing window for observing the illuminated object and a sucking part. A first sucking tube line inserted through the insertable part and leading to the operating part is connected at one end to the sucking part and at the other end to a suction switching part operating the suction from the sucking part. A second sucking tube line of an inside diameter larger than of the first sucking tube line is connected to the suction switching part so as to make the suction from the sucking part through the suction switching part.

5 Claims, 3 Drawing Sheets

ENDOSCOPE

FIELD OF THE INVENTION

This invention relates to an endoscope having sucking tube lines large in the sucking capacity.

BACKGROUND OF THE INVENTION

Recently, there is extensively used an endoscope whereby an elongated insertable part can be inserted into a body cavity to observe organs within the body cavity or various therapeutic treatments can be made, as required, by using a treating tool inserted through a treating tool channel.

Generally, there are provided sucking tube lines for sucking and removing a mucus, dirt and blood within a body cavity. Such sucking tube lines are divided into a first tube on the upper stream side from the operating part to the insertable part tip part of an ordinary endoscope and a second tube on the lower stream side from the operating part to the connector connected to the universal cord at the end. These tubes are connected at the respective ends positioned within the operating part to a suction switching part provided in the operating part and the second tube is connected at the other end to a suction pump so that a suction may be made by operating the suction switching part.

Conventionally, as disclosed, for example, in a U.S. Pat. No. 4,562,830, in such sucking tube lines, the inside diameter of the first tube and the inside diameter of the second tube have been equal to each other.

Now, the dirt and mucus must be sucked so quickly as to reduce the inspecting time to make the pain of the patient as small as possible. As a quickly sucking means, it is considered to increase the sucking capacity of the suction pump and further to enlarge the inside diameter of the sucking tube to make the resistance of the tube as small as possible. However, there are problems that, in case the sucking capacity of the suction pump is increased, the size of the pump will become large and the power consumption of the pump will increase. Also, in case the inside diameter of the sucking tube is made large, the outside diameter of the endoscope insertable part provided with this sucking tube will become large and a great pain will be given to the patient when the insertable part is inserted into the body cavity. Further, in case the inside diameter of the tube on the upper stream side is large, the sucked solid will clog the lower stream tube and no subsequent suction will be made.

OBJECT AND SUMMARY OF THE INVENTION

An object of the present invention is to provide an endoscope whereby the resistance of sucking tube lines can be made as low as possible to obtain a maximum suction amount and the impurities sucked o the upper stream side can be prevented from clogging the lower stream side.

In an endoscope of the present invention, a first suction tube line is inserted through the tip part of an insertable part from a suction switching part and a second suction tube line having an inside diameter larger than the inside diameter of the first suction tube line is inserted through the lower stream side leading to the rear end of a connecting cable from the above mentioned suction switching part.

That is to say, the inside diameter of the second sucking tube line on the lower stream side from the suction switching part is made larger than on the upper stream side so as to make the tube line resistance on the lower stream side as small as possible.

The other features and advantages of the present invention will become apparent enough with the following explanation.

BRIEF DESCRIPTION OF THE DRAWINGS

FIGS. 1 to 4 relate to an embodiment of the present invention.

FIG. 1 is an explanatory view of the internal formation of an endoscope.

FIG. 2 is an explanatory view of the formation of a water feeding tube and air feeding tube.

FIG. 4 is an explanatory view of the formation of a suction switching part.

DETAILED DESCRIPTION OF PREFERRED EMBODIMENTS OF THE INVENTION

An embodiment of the present invention shall be explained in detail in the following with referents the drawings.

Figure 1:
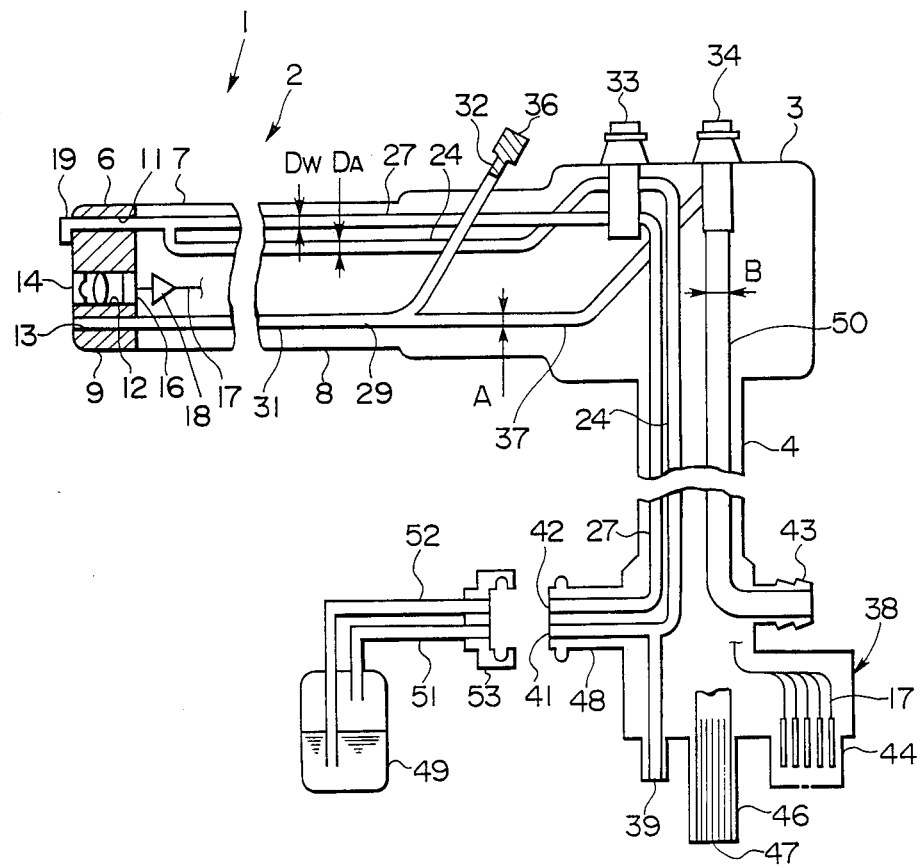

In FIG. 1, an endoscope 1 comprises an elongated insertable part 2, a thick operating part 3 connected to this insertable part 2 on the rear end side and a light guide and signal cable 4 extended from the side of this operating part 3.

A rigid tip part 6 is provided on the tip side of the above mentioned insertable part 2. A curvable part 7 is provided on the rear side adjacent to this tip part 6. Further, a flexible part 8 is provided in the rear of this curvable part 7.

The above mentioned tip part 6 is provided with a tip body 9 substantially columnally formed of a rigid material. This tip body 9 is provided in the lengthwise direction of the insertable part 2 with an air and water feeding channel through hole 11, observing through hole 12, forceps channel through hole 13 and illuminating through hole (not illustrated).

An objective lens system 14 is provided in the front part of the above mentioned observing through hole 12. Such solid state imaging device as a charge coupled device (mentioned as a CCD hereinafter) 16 photoelectrically converting an observed image is provided in the image forming position of this objective lens system. A signal line 17 is extended out of this CCD 16 at the rear end and is connected to a preamplifier 18 so as to be able to output a photoelectrically converted picture image signal.

Figure 2:
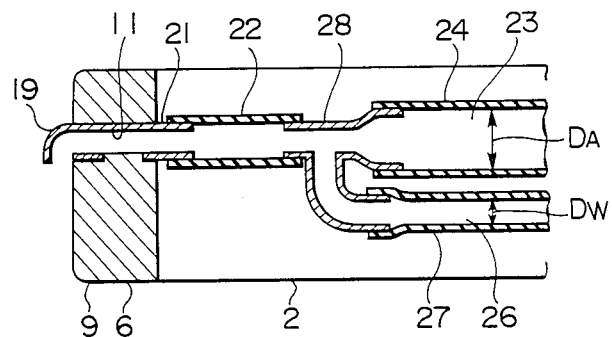

As shown in FIG. 2, an air and water feeding nozzle 19 is provided in the front part of the above mentioned air and water feeding channel through hole 11 so as to be able to wash a blood, mucus and the like deposited on the front end surface of the above mentioned objective lens system 14. A connecting pipe 21 is fitted and fixed to this air and water feeding channel through hole 11 in the rear end part and is connected with an air and water feeding tube 22. A branch pipe 28 connected with an air feeding tube 24 forming an air feeding channel 23 and a water feeding tube 27 forming a water feeding channel 26 is provided at the rear end of this air and water feeding tube 22 so that a washing liquid fed through the water feeding tube 27 may be sprayed by a gas fed through the air feeding tube 24.

By the way, the relation between the inside diameter DW of the water feeding tube 27 and the inside diameter DA of the air feeding tube 24 is DA>DW so that, by throttling the air feeding channel 24 in the branch pipe 28, the washing liquid may be more finely sprayed and the amount of water drops deposited on the surface of the objective lens system 14 may be reduced.

A forceps channel tube 31 forming a forceps channel 29 is connected to the above mentioned forceps channel through hole 13.

A forceps part 32, air and water feeding switching part 33 and suction switching part 34 are provided on the side of the above mentioned operating part. The forceps part 32 communicates with the above mentioned forceps channel tube 31 forming the forceps channel 29 and is closed with a forceps plug 36.

The above mentioned air and water feeding switching part 33 is provided in the tube line of the above mentioned air feeding tube 24 and water feeding tube 27 so that, by operating the air and water feeding switching part 33, the air feeding channel 23 and water feeding channel 26 may communicate with each other and the washing liquid sprayed by the air and water feeding nozzle 19 may be delivered. A first sucking tube 37 having an inside diameter A and branched from the forceps channel tube 31 connected to the above mentioned forceps part 32 is connected to the suction switching part 34 and a sucking tube line on the upper stream side is formed of the forceps channel tube 31 which is also a sucking tube line and the above mentioned sucking tube 37.

A connector part 38 is provided in the rear end part of the above mentioned light guide and signal cable 4 and comprises a first air feeding mouthpiece 39, a second air feeding mouthpiece 41 communicating with this first air feeding mouthpiece 39 within the connector part 38, a water feeding mouthpiece 42 provided near this second air feeding mouthpiece 41, a sucking mouthpiece 43, a signal connector 44 connected to the above mentioned pre-amplifier 18 through the signal line 17 and a light guide mouthpiece 46 connected with a light guide inserted into an illuminating through hole (not illustrated) provided in the tip part 6 and feeding an illuminating light into a body cavity.

The first air feeding mouthpiece 39 will be connected to an air feeding pump contained in a light source apparatus (not illustrated) in case the connector part 38 is connected to the light source apparatus (not illustrated).

The air feeding tube 24 communicating with the first air feeding mouthpiece 39 and second air feeding mouthpiece 41 within the connector part 38 is inserted through the light guide and signal cable 4 together with the water feeding tube 27 connected to the water feeding mouthpiece 42 and is connected to the above mentioned air and water feeding switching part 33.

The sucking mouthpiece 43 is to be connected to a suction pump (not illustrated) through a sucking tube (not illustrated) and is connected to the above mentioned suction switching part 34 through a second sucking tube 50 as a lower steam side sucking tube line having an inside diameter B larger than the inside diameter A of the first tube 37 inserted through the operating part 3, light guide and signal cable 4. That is to say, the relation between the inside diameter A of the first sucking tube 37 and the inside diameter B of the second sucking tube 50 is A<B.

Figure 4:
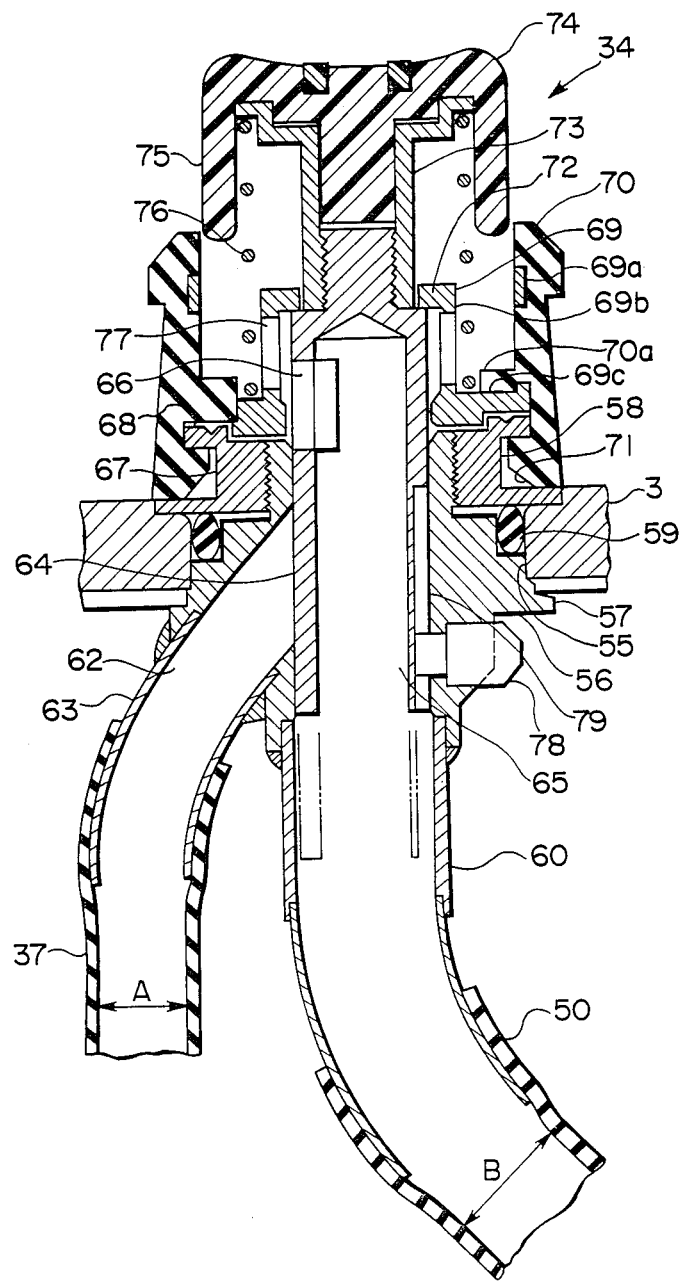

The second air feeding mouthpiece 41 and water feeding mouthpiece 42 form a connector receiving part 48 so that a connector 53 provided in the tip part of an air feeding tube 51 and water feeding tube 52 extended out of a water feeding tank 49 may be simultaneously connected The above mentioned suction switching part 34 is formed as in FIG. 4.

A fitting hole 55 is made in the outer wall of the operating part 3, a cylinder 56 as a valve seat body is fitted to this fitting hole 55, is projected at the outer end out of the operating part 3 and has a flange 57 formed on the outer periphery at the inner end and a fitting ring 58 is screwed to the cylinder 56 on the outer periphery at the outer end so that the cylinder 56 may be fitted and fixed by holding the operating part 3 on the outer wall between the fitting ring 58 and flange 57. By the way, such water-tight member 59 as, for example, an O-ring is provided between the inner peripheral surface of the fitting hole 55 and the outer peripheral surface of the cylinder 56 to secure the water-tightness between the fitting hole 55 and the outer wall of the operating part 3. The second sucking tube 50 having an inside diameter B is connected to the cylinder 56 at the inner end through a first connecting tube 60. Further, an aperture 62 opening within the cylinder 56 is formed in the side wall of the cylinder 56 and is connected with the first sucking tube 37 having an inside diameter A through a second connecting tube 63. A switching controlling piston 64 is vertically movably fitted within the cylinder 56. A hollow hole 65 opening at the inner end is formed axially within this piston 64 and communicates outside on the outer inner peripheral surface through an aperture 66 made in the central side wall of the piston 64 so that, when the piston 64 is in a standby position, this aperture 66 will project above the outer end of the cylinder 56 but, when the piston 64 is pushed in, the aperture 66 will be opposed to coincide and communicate with the aperture 62 of the cylinder 56.

The above mentioned fitting ring 58 has a groove 67 formed peripherally on the outer peripheral surface and a flange 68 formed outside this groove 67. This flange 68 is removably fitted with a butting member 69 made of a metal, formed concentrically of an outer cylinder 69a and inner cylinder 69b and integrally connected through a connecting bottom wall 69c between the outer cylinder 69a and inner cylinder 69b at the ends. This outer cylinder 69a has a substantially cylindrically formed elastic member 70 integrally fitted and fixed by insert molding. An engaging projection 71 elastically closely fitting in the groove 67 provided on the above mentioned flange 68 is formed at the end of this elastic member 70. A butting part 72 protruding inside in the diametral direction is formed at the outer end of the inner cylinder 69b so that the piston 64 in the standby position may contact on the outer end surface with the inner end surface of this butting part 72 to regulate the standly position. The piston 64 is screwed at the upper end with a connecting tube 73 having a flange at the outer end. Further, an operating button 74 made of a comparatively hard plastic is fitted to the outer end of this connecting tube 73. A falling cylindrical wall 75 is provided on the peripheral edge of this operating button 74 so as to be contained within the elastic member 70 and contact the outer end surface of a projection 70a provided on the inner peripheral surface of the above mentioned elastic member 70 in case the piston 64 is pushed in.

A coil spring 76 as a piston 64 energizing member is interposed between the flange provided at the outer end of the above mentioned connecting tube 73 and the above mentioned connecting bottom wall 69c so as to be energized in case the piston 64 is pushed in.

A plurality of leaking holes 77 are made in the diametral direction in the wall of the above mentioned inner cylinder 69b so as to communicate with the hollow hole 65 through the aperture 66 of the piston 64 in case the piston 64 is in the standby position. In order to prevent the rotation of the piston 64, a guide pin 78 projecting in the diametral direction out of the inner wall surface of the cylinder 56 is provided on the side wall of the cylinder 56 so as to be engaged at the tip with a groove 79 provided in the axial direction on the outer peripheral surface of the piston 64.

In case the above mentioned suction switching part 34 is in a standby position, the aperture 62 of the cylinder 56 will be closed by the outer peripheral surface of the piston 64, therefore the first sucking tube 37 and second sucking tube 50 will be intercepted from each other and the suction to the forceps channel tube 31 through the first sucking tube 37 will no longer act. However, as the hollow hole 65 of the piston 64 communicates with the outside through the aperture 66 and plurality of leaking holes 77, outside air will be sucked in.

In the case of sucking, when the operating button 74 is pushed in until the wall 75 contacts on the inner end surface with the projection 70a, the aperture 66 of the piston 64 will communicate with the aperture 62 of the cylinder 56 and the first sucking tube 37 and second sucking tube 50 will communicate with each other through the apertures 66 and 62 but will be intercepted from the outside. Therefore, while preventing the suction of outside air, a suction will be made through the first sucking tube 37 and second sucking tube 50.

The operation of the endoscope formed as mentioned above shall be explained.

When the insertable part 2 is inserted into a body cavity, the tip part 6 is led to a part to be treated while observing with a monitor (not illustrated) and a treating tool is inserted through the forceps part 32 to make a therapeutic treatment, a blood, dirt, mucus and the like will be deposited on the objective lens system 14 by this treatment. In case a desired observed image is not obtained, when the air and water feeding switching part 33 is operated, a gas will be made to flow into the air feeding channel and a washing liquid will be made to flow into the water feeding channel. These flowing gas and washing liquid will be mixed in the branch tube 28.

In such case, as the inside diameter DA of the air feeding channel 23 is larger than the inside diameter DW of the water feeding channel 26, a larger amount of the gas will be fed and further, as the branch tube 28 is throttled, the flow velocity of the gas will be increased, the washing liquid will be more finely sprayed and will be delivered out of the air and water feeding nozzle 19. As this washing liquid is finely sprayed, water drops will not be deposited on the front end surface of the objective lens 14 and a favorable visual field will be able to be obtained. When the forceps part 32 of the operating part 3 is then closed with the forceps plug 36 and the suction switching part 34 is operated, the washing liquid, mucus, blood and the like delivered into the body cavity will be sucked. In the operation of the suction switching part 34 when the operating button 74 is pushed in, the first sucking tube 37 having the inside diameter A and the second sucking tube 50 having the inside diameter B will be made to communicate with each other. A suction pump (not illustrated) is connected to the sucking mouthpiece 43 communicating with the second sucking tube 50. The washing liquid, mucus, dirt and blood will be sucked by this suction pump. In such case, as the inside diameter B of the second sucking tube 50 is larger than the inside diameter A of the first sucking tube 37, the tube line resistance of the sucking tube line from the second sucking tube 50 to the suction pump (not illustrated) will be able to be made smaller and the suction amount of the suction pump (not illustrated) will be able to be made larger. As the suction amount becomes larger, the dirt and mucus will be able to be quickly sucked. Further, the solid sucked within the first sucking tube 37 will not clog the second sucking tube 50.

Figure 3A:
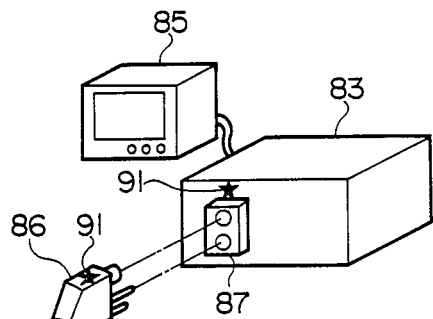
FIG. 3(a) is an explanatory view of the formation of an endoscope apparatus of a mosaic filter system.
Figure 3B:
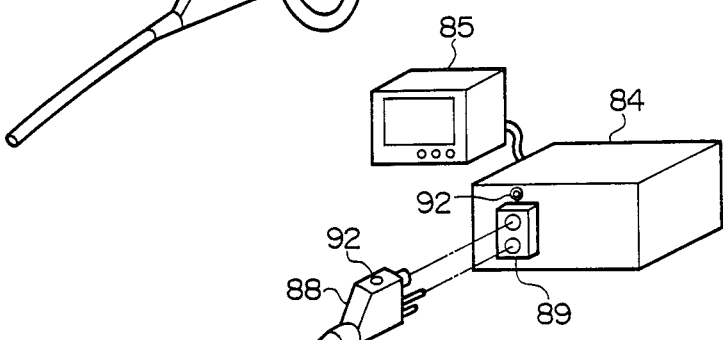
FIG. 3(b) is an explanatory view of the formation of an endoscope apparatus of a frame sequential system.
Figure 3B:
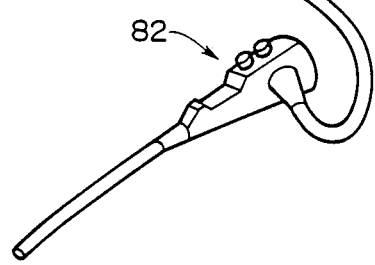

By the way, in FIG. 3, the electronic endoscope (which shall be mentioned as an electronic scope hereinafter) using a CCD may be an RGB frame sequential system electronic scope 81 or a mosaic filter system electronic scope 82. The RGB frame sequential system and mosaic filter system are different from each other in the CCD driving system and signal processing circuit and are therefore connected respectively to separate video processors to display observed picture images in monitors 85. That is to say, the RGB frame sequential system video processor 83 will be connected to the RGB frame sequential system electronic scope 81 and the mosaic filter system video processor 84 will be connected to the mosaic filter system electronic scope 82. Further, the scope side connector 86 of the RGB frame sequential system electronic scope 81 and the VP side connector 87 of the RGB frame sequential system video processor 83 are provided with, for example, star marks 91 as discriminating marks. The scope side connector 88 of the mosaic filter system electronic scope 82 and the VP side connector 89 of the mosaic filter system video processor 84 are provided with, for example, double circle marks 92 as discriminating marks. By thus providing the connector parts with discriminating marks, the electronic scope and video processor of the same imaging system can be easily selected and connected. Also, even in the case of the same imaging system of the RGB frame sequential system or mosaic filter system, by the difference of the kind of the CCD, for example, the number of pixels, the driving system and signal processing circuit will be different. Therefore, the electronic scopes may be provided respectively with discriminating marks corresponding to the kinds of the CCD so as to be able to be respectively discriminated and easily selected to be used.

By the way, in addition to the discriminating marks, the scope side connector and VP side connector may be made in the same color so as to be able to be discriminated.

As in this embodiment, as the inside diameter B of the second sucking tube 50 on the lower stream side from the suction switching part 34 inserted through the light guide and signal cable 4 from the operating part 3 not inserted into a body cavity is made larger than the inside diameter A of the first sucking tube 37 on the upper stream side from the suction switching part 34, the tube line resistance of the second sucking tube 50 can be reduced and the resistance of the entire tube line including the first and second tubes 37 and 50 can be made low. Therefore, without enlarging the outside diameter of the endoscope insertable part 2, even in the case of making a suction by operating the suction switching part 34, a suction out of the endoscope tip part 6 can be quickly and favorably made.

Also, as the inside diameter of the second sucking tube 50 is larger than the inside diameter of the first sucking tube 37, the sucked solid will not clog the second sucking tube 50.

By the way, in this embodiment, the forceps channel tube 31 is also the first sucking tube 37 but they may be made separate and inserted through the insertable part.

The present invention may be applied not only to electronic scopes but also fiber scopes.

As explained above, according to the present invention, a maximum suction amount can be obtained by reducing the resistance of the sucking tube lines to be as low as possible and the impurities sucked on the upper stream side can be prevented from cloging the lower stream side.

What is claimed is:

1. An endoscope comprising:
   an insertable part inserted into a body cavity and having in the front end part an illuminating window illuminating an observed part and an observing window for observing the illuminated object;
   an operating part provided in the rear of said insertable part;
   a first sucking tube line communicating with a sucking part provided at the front end of said insertable part, inserted through said insertable part and leading to said operating part;
   a suction switching part provided in said operating part, communicating with said first sucking tube line and making a sucking operation from said sucking port; and
   a second sucking tube line communicating with said first sucking tube line through said suction switching part and having an inside diameter larger than the inside diameter of said first sucking tube line.

2. An endoscope according to claim 1 wherein said first sucking tube line is also a forceps channel.

3. An endoscope according to claim 1 further comprising a washing nozzle washing said observing window at the front end of the insertable part.

4. An endoscope according to claim 3 wherein said washing nozzle has an air feeding tube feeding a gas and a water feeding tube feeding a liquid connected with each other so as to deliver a washing liquid of a mixture of a liquid and gas as sprayed and the inside diameter of the air feeding tube is larger than the inside diameter of the water feeding tube.

5. An endoscope according to claim 1 wherein said second sucking tube line is connected to said operating part and is inserted through a connecting cable provided with a light guide transmitting an illuminating light at least to said illuminating window.

* * * * *